(12) United States Patent
Castro Retamal et al.

(10) Patent No.: US 9,567,610 B2
(45) Date of Patent: Feb. 14, 2017

(54) **USE OF *BOTRYTIS CINEREA* FOR OBTAINING GOLD NANOPARTICLES**

(71) Applicant: Universidad de Santiago de Chile, Estacion Central (CL)

(72) Inventors: Miguel Castro Retamal, Santiago (CL); Antonio Castillo Nara, Santiago (CL)

(73) Assignee: Universidad de Santiago de Chile, Estacion Central, Santiago (CL)

( * ) Notice: Subject to any disclaimer, the term of this patent is extended or adjusted under 35 U.S.C. 154(b) by 0 days.

(21) Appl. No.: 14/389,694

(22) PCT Filed: Mar. 28, 2013

(86) PCT No.: PCT/CL2013/000019
§ 371 (c)(1),
(2) Date: Sep. 30, 2014

(87) PCT Pub. No.: WO2013/143017
PCT Pub. Date: Oct. 3, 2013

(65) Prior Publication Data
US 2015/0072392 A1    Mar. 12, 2015

(30) Foreign Application Priority Data

Mar. 30, 2012 (CL) .................................. 789-2012

(51) Int. Cl.
*C12P 3/00* (2006.01)
*B82Y 30/00* (2011.01)

(52) U.S. Cl.
CPC . *C12P 3/00* (2013.01); *B82Y 30/00* (2013.01)

(58) Field of Classification Search
None
See application file for complete search history.

(56) References Cited

PUBLICATIONS

Retamal et al., Biosíntesis de nanopartículas de plata y oro por el hongo fitopatógeno Botrytis cinerea, Congreso Latinoamericano de Microbiologia, Oct. 28-Nov. 1, 2012, Poster 1118-1; Machine Translation.*
Balagurunathan et al.; "Biosynthesis of gold nanoparticles by actinomycete Streptomyces viridogens strain HM10"; Indian Journal of Biochemistry & Biophysics; vol. 48, 2011; pp. 331-335.
Castro Retamal et al.; "Biointesis de nanoparticulas de plata y oro por el hongo fitopatogeno Botrytis cinerea"; Congreso Latinoamericano de Microbiologia; 2012; pp. 1; XP002698671.
Duran et al.; "Mechanistic aspects in the biogenic synthesis of extracellular metal nanoparticles by peptides, bacteria, fungi, and plants"; Applied Microbiology and Biotechnology; vol. 90, 2011; pp. 1609-1624.
International Search Report; PCT/CL2013/000019; Jun. 25, 2013; 3 pp.
Moudato et al.; "Biosynthesis of crystalline silver and gold nanoparticles by extremophilic yeasts"; Bioinorganic Chemistry and Applications; 2011; pp. 108.
Narayanan et al.; "Biological Synthesis of Metal Nanoparticles by Microbes"; Advances in Colloid and Interface Science; vol. 156; 2010; pp. 1-13.
Narayanan et al.; "Green synthesis of biogenic metal nanoparticles by terrestrial and aquatic phototrophic and heterotrophic eukaryotes and biocompatible agents"; Advances in Colloid and Interface Science; vol. 169, 2011; pp. 59-79.
Smitha et al.; "SERS and antibacterial active green synthesized gold nanoparticles"; Plasmonics; vol. 7, 2012; pp. 515-524.
Solmczynski et al.; "Production and characterization of laccase from Botrytis cinerea 61-34"; Appled and Environmental Microbiology; vol. 61, 1995; pp. 907-912.
Tikariha et al.; "Biosynthesis of gold nanoparticles, scope and application: A review"; International Journal of Pharmaceutical Sciences and Research; vol. 3; 2012; pp. 1603-1615.
Written Opinion; ; PCT/CL2013/000019; Jun. 25, 2013; 6 pp.

* cited by examiner

*Primary Examiner* — Karen Cochrane Carlson
*Assistant Examiner* — Jennifer M. H. Tichy
(74) *Attorney, Agent, or Firm* — Fish & Richardson P.C.

(57) ABSTRACT

The present invention is related to the use of *Botrytis cinerea* strains, its spores, hyphae mycelium, sclerotia, intra and/or extracellular organic molecules, such as proteins, nucleic acids, polysaccharides, lipids and secondary metabolites for the biosynthesis of gold nanoparticles (AuNps). In general terms, the present invention is focused to use *B. cinerea* strains and/or molecules generated by this organism for the biological synthesis of AuNps, being then the field of application, the synthesis of nanomaterials, specifically AuNps using the phytopathogenic fungus *B. cinerea* and/or its intra or extracellular proteins purified individually or in combination thereof or any of other intra and/or extracellular molecule produced by this organism as a biological system of synthesis. The metallic nanoparticles are used in various applications including: semiconductors, photoluminescence, biomedicine, imaging for the medical diagnostic, catalysts (dispersed and supported) and in therapies against some types of neoplasia (cancer), among others.

1 Claim, 2 Drawing Sheets

USE OF *BOTRYTIS CINEREA* FOR OBTAINING GOLD NANOPARTICLES

FIELD OF THE INVENTION

Figure 1:
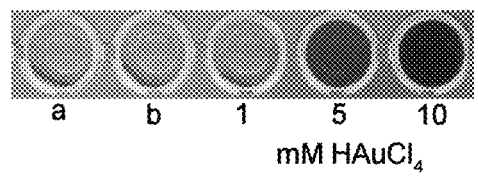
Figure 2:
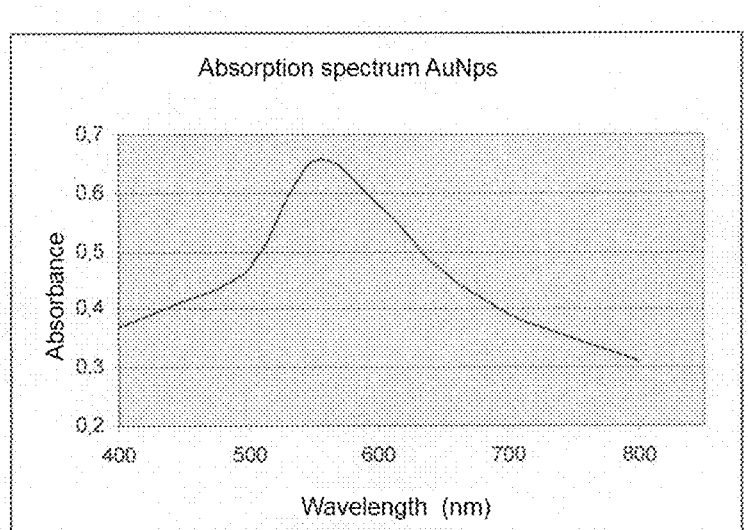
Figure 3:
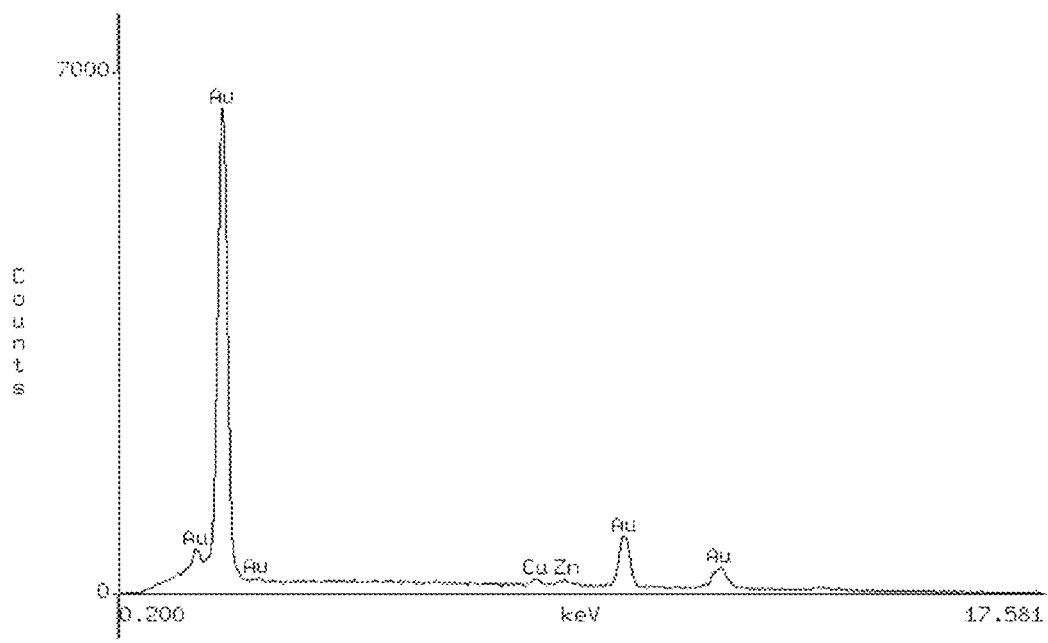
Figure 4:
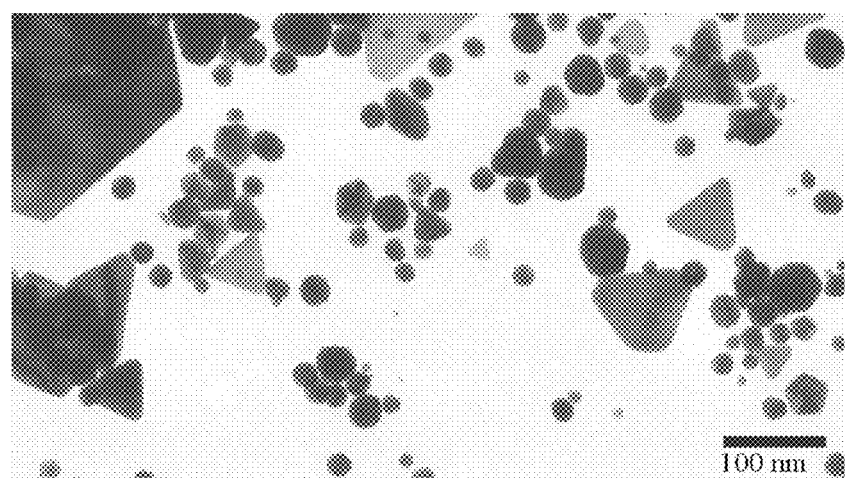

The present invention relates to the use of *Botrytis cinerea* strains, its spores, hyphae, mycelium and/or sclerotia and/or molecules generated by this organism, such as proteins, nucleic acids, polysaccharides, lipids and secondary metabolites, for the biosynthesis of gold nanoparticles (AuNps). In general terms, the present invention is focused to use *B. cinerea* strains and/or molecules generated by this organism for the biological synthesis of AuNps. Therefore, the field of application is centered in the synthesis of nanomaterials, specifically AuNps using the phytopathogenic fungus *B. cinerea* and/or its intra or extracellular proteins purified individually or in combination thereof or any of other molecule produced by this organism as a biological system of synthesis.

The metallic nanoparticles are used in various applications including: semiconductors, photoluminescence, biomedicine, imaging for the medical diagnostic, catalysts (dispersed and supported) and in therapies against some types of neoplasia (cancer), among others.

BACKGROUND OF THE INVENTION

The nanoparticles are structures with a size ranging from 1 to 100 nanometers and are especially attractive due to its optical, chemical, photoelectrochemical and electrical properties (Wilson M., Kannangara K., Smith G, Simmons M., Raguse B. Nanotechnology: Basic Science and Emerging Technologies. Chapman and Hall/CRC 2002; Jain, P. K., Huang, X., El-Sayed, I. H. El-Sayed, M. A. 2008. Noble metals on the nanoscale: optical and photothermal properties and some applications in imaging, sensing, biology and medicine. A of Chem Res. 41:1578-1586).

The synthesis of nanoparticles of different compositions and sizes is a field of investigation of great interest in the last years. Currently, the large scale production of AuNPs is carried out by chemical processes, which require the use of reducing agents to generate the particles from soluble gold salts. There are also physical processes, which require operating at reduced pressures and high temperatures. In both cases associated with AuNPs production, are produced chemical toxic compounds, due to the reactive agents and the operating conditions of the signaled systems; which present problems related to stability, aggregation and control of the desired size of the generated nanoparticles (Sau T. K., Murphy C. J. 2004. Room temperature, high-yield synthesis of multiple shapes of gold nanoparticles in aqueous solution. J Am Chem Soc 126:8648-8649).

Given the relevance of this topic worldwide, indispensable is the need to implement alternative and efficient processes for obtaining metallic nanoparticles that are "environmentally friendly" without requiring high quantities of energy. In this regard, biological systems are good candidates to do this. Currently, there are various publications on this topic, specifically related to the capacity of some organisms to generate these structures including bacteria and fungi (Brown S, Sarikaya M, Johnson E A. 2000. Genetic analysis of crystal growth. J Mol Biol 299: 725-735; Nair B, Pradeep T. 2002. Coalescence of nanoclusters and formation of submicron crystallites assisted by *Lactobacillus* strains. Cryst Growth Des 2: 293-298; Husseiny M I, Abd El-Aziz M, Badr Y, Mahmoud M A. 2007. Biosynthesis of gold nanoparticles using *Pseudomonas aeruginosa*. Spectrochimica Acta Part A 67: 1003-1006; Narayanan K B, Sakthivel N. 2010. Biological synthesis of metal nanoparticles by microbes. Adv Colloid Interface Sci 156: 1-13; Thirumurugan G, Veni V S, Ramachandran S, Rao J V, Dhanaraju M D. 2011. Superior wound healing effect of topically delivered silver nanoparticle formulation using eco-friendly potato plant pathogenic fungus: synthesis and characterization. J Biomed Nanotechnol. 7: 659-66; Mourato A, Gadanho M, Lino A R, Tenreiro R. 2011. Biosynthesis of crystalline silver and gold nanoparticles by extremophilic yeasts. Bioinorg Chem Appl. 2011: 546074; Balagurunathan R, Radhakrishnan M, Rajendran R B, Velmurugan D. 2011. Biosynthesis of gold nanoparticles by actinomycete *Streptomyces viridogens* strain HM10. Indian J Biochem Biophys 48: 331-335; Tikariha, S.; Singh, S.; Banerjee, S.; Vidyarthi, A. S. 2012. Biosynthesis of gold nanoparticles, scope and application: A review. IJPSR 3: 1603-1615).

The probable mechanisms by which peptides, bacteria, fungi, and plants catalyze the extracellular synthesis of metal nanoparticles have been recently revised (Durán N, Marcato P D, Durán M, Yadav A, Gade A, Rai M. 2011. Mechanistic aspects in the biogenic synthesis of extracellular metal nanoparticles by peptides, bacteria, fungi, and plants. Appl Microbiol Biotechnol 90: 1609-1624).

*B. cinerea* is a phytopathogenic fungus which infects a large number of vegetal species of great economic importance including fruit trees, ornamental plants and vegetables. This fungus produces a disease known as grey mold generating a serious problem on pre and postharvest in strawberries, raspberries, apples, pears, chestnuts, kiwi and grapes among others. In the grapevine, this fungus produces the bunch rot, (van Kan J. A. 2006. Licensed to kill: the lifestyle of a necrotrophic plant pathogen. Trends Plant Sci. 11, 247-253; Elad, Y., Williamson, B., Tudzynski, P. and Delen, N. eds. 2007. *Botrytis: Biology, Pathology and Control. The Netherlands*: Kluwer Academic Publishers).

Traditionally, *B. cinerea* has been studied with the objective of generating strategies to allow its control, and thus, to reduce the economic loss associated with the infections generated by the fungus. Up to today, there are no studies in nanotechnology field where cultures, propagules or molecules of *B. cinerea* are used in the process of synthesis of metallic nanoparticles. Our results show that *B. cinerea* in liquid medium is able to catalyze the synthesis of gold nanoparticles at room temperature from a solution of $HAuCl_4$. The formation of nanoparticles is verified by the change of color of the reaction solution from pale yellow to reddish o purple. Moreover, the solutions containing the nanoparticles present a maximum of absortion at 540 nm, characteristic of the presence of this type of structures (Castro M E, Bravo M, Castillo A. 2012. Biosíntesis de nanopartículas de plata y oro por el hongo fitopatógeno *Botrytis cinerea*. XXI Congreso Latinoamericano de Microbiologia. Santos, Brasil. 28 de Octubre-1 de Noviembre).

Respect to the intellectual property, the patents related to synthesis of metallic nanoparticles mostly consist of the use of chemical processes for the synthesis of these structures, some of them allow the production of particles of a certain size and morphology. This is the case of the U.S. Pat. No. 6,929,675 in which is described a chemical system for the generation of copper, silver and gold nanoparticles. In specific relation with the AuNps, it is also possible to find some publications, like the patent US 20070125196, in which is disclosed the synthesis of AuNPs in a size ranging from 30 to 90 nm using a aqueous medium containing sodium acrylate and also the publication US 20060021468 in which is described a chemical process to control the uniformity of the generated particles.

Finally, it should be noted that although there are patents related to the use of biological systems for the synthesis of AuNps, there are currently no patents describing the use of *B. cinerea* or the molecules produced by said fungus for such purposes. In this context, the patent of greatest similarity is the patent published by a researcher of University of Illinois in the year 2010 (Publication US No. 20100055199), in which is described the use of the fungus *Trichoderma reesei* for the synthesis of AuNps.

SUMMARY OF THE INVENTION

The present invention corresponds to the synthesis of AuNps mediated by the filamentous ascomycete *B. cinerea* and/or molecules secreted by the fungal mycelium. Because of the above, the process can be carried out using directly the fungus or its molecules in an isolated manner.

BRIEF DESCRIPTION OF THE FIGURES

FIG. 1. Synthesis of extracellular AuNps by *B. cinerea. B. cinerea* culture supernatant incubated with $HAuCl_4$ in different wells of ELISA microplates. (a) Culture medium without inoculation, (b) culture medium obtained from cultures of *B. cinerea*, (1, 5 and 10) culture medium obtained from cultures of *B. cinerea* in presence of $HAuCl_4$ 1, 5 and 10 mM, respectively.

FIG. 2. Absorption spectrum of the AuNps generated by *B. cinerea* culture supernatants. A maximum of absorption is observed at 550 nm approximately.

FIG. 3. EDS Spectrum of the gold particles generated by *B. cinerea*. Signals corresponding to the presence of the gold element as a constituent of the nanoparticles are observed.

FIG. 4. Transmission electron microscopy of the gold particles generated by *B. cinerea*. A great diversity of sizes and morphologies of particles is observed. The bar at the bottom right corresponds to 100 nm.

DESCRIPTION OF A PREFERRED EMBODIMENT OF THIS INVENTION

Process specifically designed to produce gold nanoparticles from filamentous fungi. This process comprises the following steps:

1. Growth of the fungal mycelium: Is cultivated in 250 mL Erlenmeyer flasks containing 50 mL of a nutritive medium containing between 0.1-1% malt extract and 0.1-1% yeast extract. The fungus was cultivated at 20° C. in darkness, and to do this, the flasks were maintained in a dark room for 10 days.

2. Generation of metallic nanoparticles: In a 500 mL Erlenmeyer flask was collected approximately 100 mL of the supernatant liquid obtained from the growth of the fungus and was incubated with $HAuCl_4.3H_2O$ (final concentration 0.5-10 mM). To do this, was added to the supernatant 0.5-10 mL of a solution of $HAuCl_4.3H_2O$ 100 mM and the 500 mL Erlenmeyer flask was incubated at a temperature ranging between 25-27° C. for a period of time ranging from 0.5 to 12 hours. The particles were retrieved by low-speed centrifugation (6,000-8,000 rpm) o by spontaneous sedimentation leaving the tubes at rest for at least 1 hour.

The material was characterized by: i) adsorption spectrum in which is observed a maximum at approximately 550 nm. ii) Transmission electron microscopy of the gold particles generated by *B. cinerea*. A great diversity of sizes (between 10-300 nm) as well as morphologies of the particles (spherical, hexagonal, triangular and polyhedral) is observed.

The invention claimed is:

1. Process for the biological synthesis of gold nanoparticles (AuNps) by *Botrytis cinerea* strains, spores, hyphae, mycelium, sclerotia and/or molecules generated by such microorganism, comprising:

a) culturing such *Botrytis cinerea* strains, spores, hyphae, mycelium or sclerotia in a nutritive medium containing between 0.1-1% malt extract and 0.1-1% yeast extract at 20° C. in darkness for at least 10 days; and separating a fungal supernatant from such nutritive medium; and b) generating gold nanoparticles by incubating the fungal supernatant with $HAuCl_4.3H_2O$, or alternatively extracting the molecules from the fungal supernatant and incubating them with $HAuCl_4.3H_2O$, for a period of time ranging from 0.5 to 12 hours, at a temperature ranging between 25-27° C. and retrieving the nanoparticles using a centrifugation speed of 6,000 to 8,000 rpm or by spontaneous sedimentation after a rest of at least 1 hour.

* * * * *